(12) United States Patent
Miyahara et al.

(10) Patent No.: US 7,955,493 B2
(45) Date of Patent: Jun. 7, 2011

(54) METHOD OF MEASURING THE NUMBER OF BACTERIA, DEVICE OF MEASURING THE NUMBER OF BACTERIA AND CELL USED IN THE DEVICE

(75) Inventors: Seiichiro Miyahara, Ibaraki (JP); Chiaki Okumura, Ibaraki (JP); Naoki Fukui, Ibaraki (JP); Megumi Akamatsu, Ibaraki (JP)

(73) Assignee: Daikin Industries, Ltd., Osaka (JP)

( * ) Notice: Subject to any disclaimer, the term of this patent is extended or adjusted under 35 U.S.C. 154(b) by 813 days.

(21) Appl. No.: 11/573,081

(22) PCT Filed: Jun. 16, 2005

(86) PCT No.: PCT/JP2005/011062
§ 371 (c)(1),
(2), (4) Date: Dec. 13, 2007

(87) PCT Pub. No.: WO2006/013679
PCT Pub. Date: Feb. 9, 2006

(65) Prior Publication Data
US 2008/0197023 A1    Aug. 21, 2008

(30) Foreign Application Priority Data
Aug. 2, 2004   (JP) .................................. 2004-225765

(51) Int. Cl.
*C12M 1/34*   (2006.01)
(52) U.S. Cl. ............. 205/777.5; 204/403.01; 435/287.5; 436/62
(58) Field of Classification Search ............. 204/403.01; 205/777.5; 435/287.5; 436/62
See application file for complete search history.

(56) References Cited

FOREIGN PATENT DOCUMENTS

| EP | 1 775 579 A1 | 4/2007 |
|---|---|---|
| JP | 63-015150 A | 1/1988 |
| JP | 03-198767 A | 8/1991 |
| JP | 05-123186 A | 5/1993 |
| JP | 10-276796 A | 10/1998 |
| JP | 2000-287699 | * 10/2000 |
| JP | 2000-287699 A | 10/2000 |
| WO | WO-2006/013617 A1 | 2/2006 |

OTHER PUBLICATIONS

Francy et al., "Comparison of methods for determining *Escherichia coli* concentrations in recreational waters", Water Research, vol. 34, No. 10, Jul. 2000, p. 2770-2778.*

(Continued)

*Primary Examiner* — Ula C Ruddock
*Assistant Examiner* — J. Christopher Ball
(74) *Attorney, Agent, or Firm* — Global IP Counselors

(57) ABSTRACT

A method of measuring the number of bacteria according to the present invention includes step (a) through step (d). First, in step (a), a to-be-measured sample (specimen) including a predetermined bacterial strain (such as *Escherichia coli* or coliform bacteria) is added to a predetermined medium (such as a medium used for a specific enzyme substrate culture medium method). In step (b), a current value flowing through the medium added with the sample is measured with an oxygen electrode at a predetermined temperature and at a predetermined constant voltage. In step (c), time required is measured for the current value that has decreased temporarily after starting the measurement of step (b) to increase thereafter to exceed a predetermined threshold value. In step (d), the initial number of bacteria of the bacterial strain included in the sample is calculated based on the time required.

12 Claims, 8 Drawing Sheets

OTHER PUBLICATIONS

Rice et al., "Efficacy of β-glucuronidase assay for identification of *Escherichia coli* by the defined-substrate technology", Applied and Environmental Microbiology, vol. 56, No. 5, May 1990, p. 1203-1205.*

Landre et al., "False-positive coliform reaction mediated by *Aeromonas* in the Colilert defined substrate technology system", Letters in Applied Microbiology, vol. 26, 1998, p. 352-354.*

* cited by examiner

F I G . 4
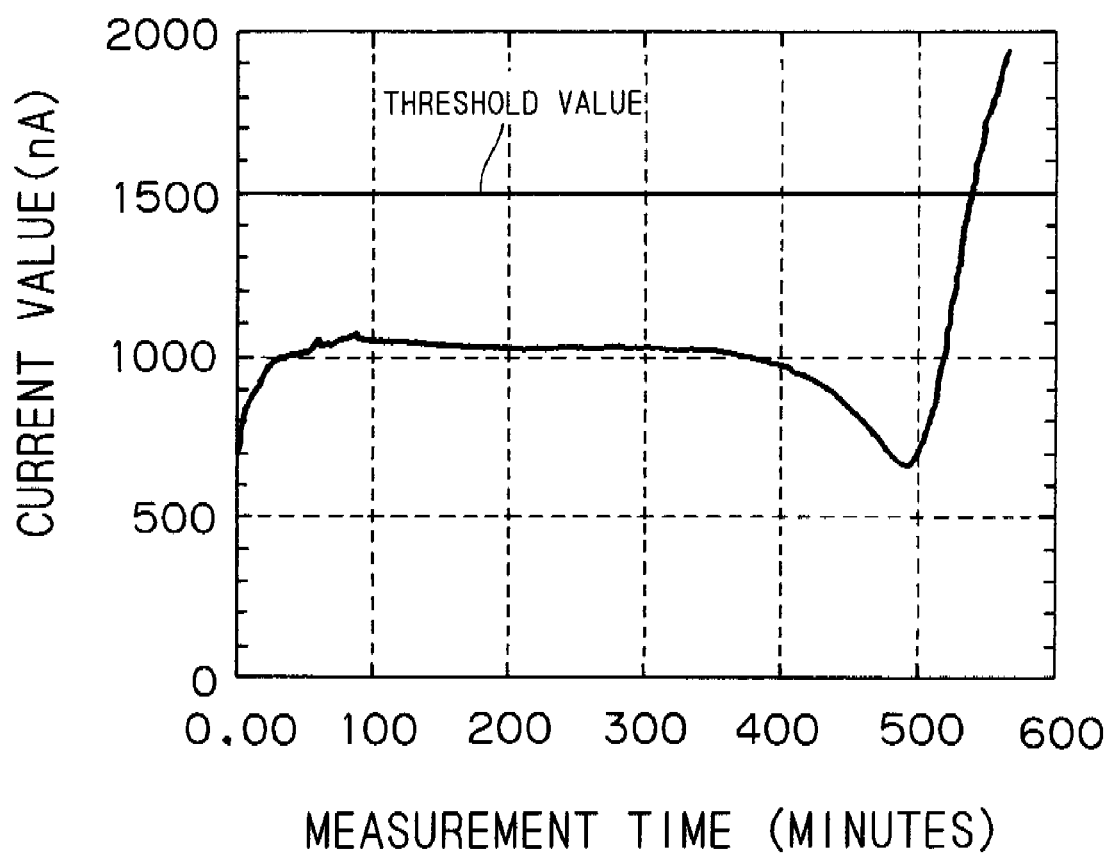

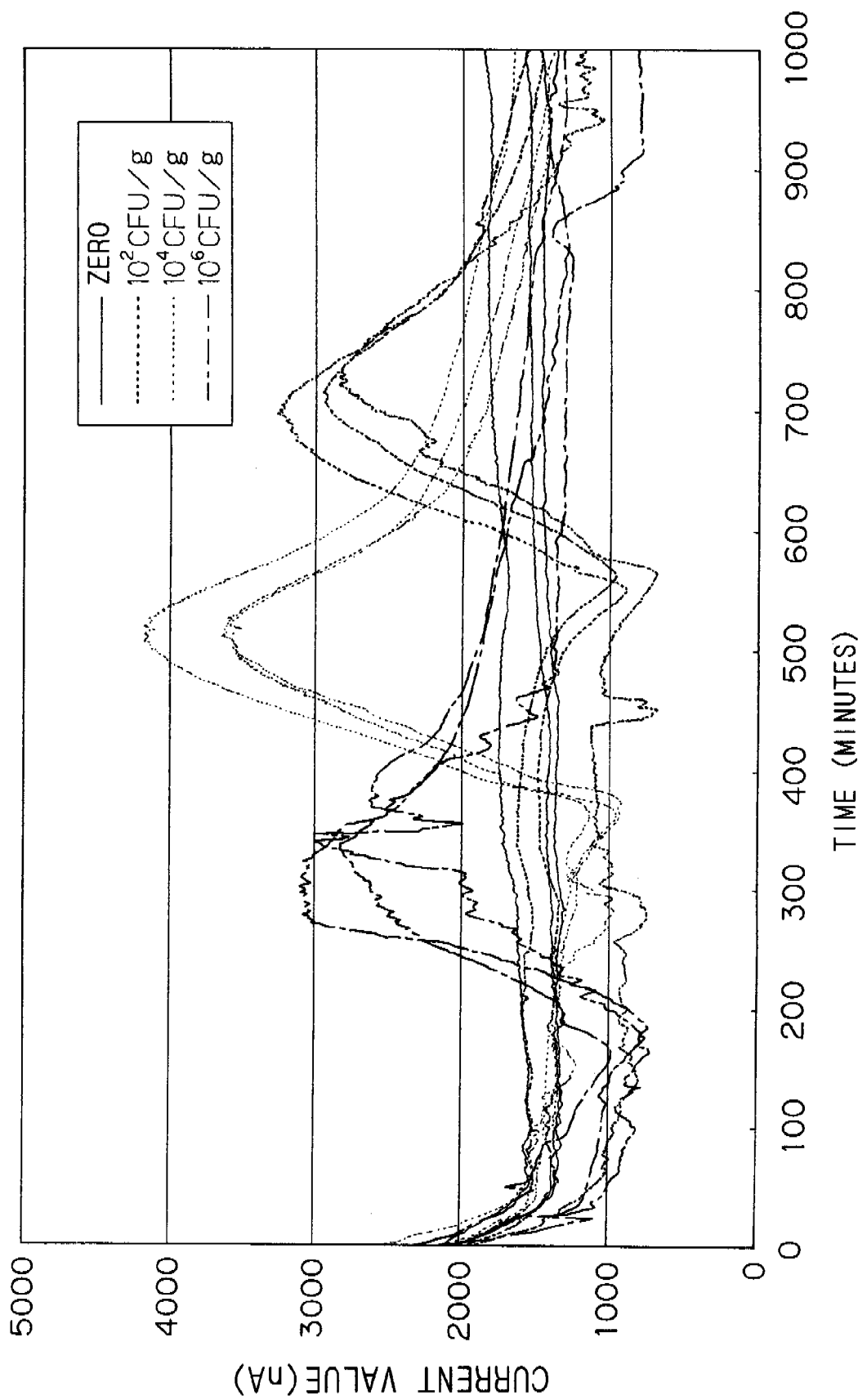

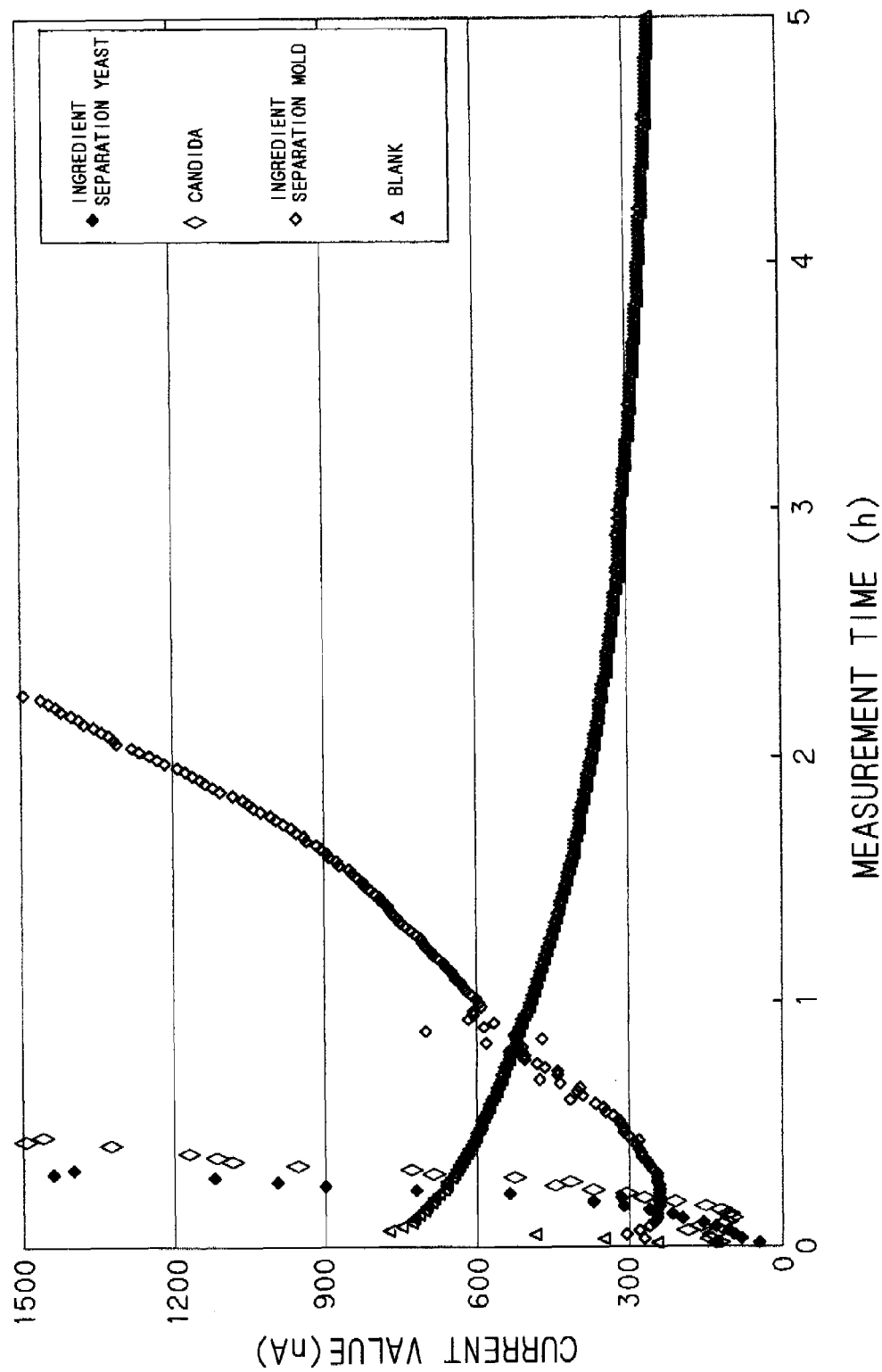

METHOD OF MEASURING THE NUMBER OF BACTERIA, DEVICE OF MEASURING THE NUMBER OF BACTERIA AND CELL USED IN THE DEVICE

CROSS-REFERENCE TO RELATED APPLICATIONS

This U.S. National stage application claims priority under 35 U.S.C. §119(a) to Japanese Patent Application No. 2004-225765, filed in Japan on Aug. 2, 2004, the entire contents of which are hereby incorporated herein by reference.

TECHNICAL FIELD

The present invention relates to methods of measuring the number of bacteria, devices of measuring the number of bacteria and cells used in the devices, and more particularly to a method of measuring the number of bacteria with an oxygen electrode, a device of measuring the number of bacteria with an oxygen electrode and a cell used in the device.

BACKGROUND ART

It is sometimes requested to measure the number of bacteria included in food for the purposes of food hygiene management and the like. A conventional method of measuring bacteria included in a specimen such as food dilutes the specimen in stages and applies them in a fixed amount on an agar medium, cultures them for about 24 hours, and visually calculates the number of derived colonies, to measure the number of bacteria. Unfortunately, this method has the need for staged specimen dilution and the need for about 24-hour culture. This resulted in the development of a method that measures the number of bacteria by measuring dissolved oxygen concentration contained in a liquid medium added with a specimen with an oxygen electrode (hereafter also called an oxygen electrode method), as is described in Japanese Patent Application Laid-Open No. 2000-287699.

In the oxygen electrode method described in Japanese Patent Application Laid-Open No. 2000-287699, the higher the dissolved oxygen concentration contained in the liquid medium, the larger amount of current is measured. Bacteria included in the specimen consume the dissolved oxygen in the liquid medium through respiration. As the dissolved oxygen concentration decreases due to the respiration of the bacteria, a current flowing through the oxygen electrode decreases. In addition, the amount of dissolved oxygen consumed depends on the initial number of bacteria included in the specimen. Namely, the larger the initial number of bacteria, the larger amount of oxygen is consumed and the faster the dissolved oxygen concentration decreases. When the dissolved oxygen concentration decreases in a short time, the current value being measured also decreases in a short time. That is, the time required for a current flowing through a liquid medium including a specimen with an unknown initial number of bacteria to decrease down to a predetermined threshold value is obtained, thereby determining the initial number of bacteria corresponding to the time required. In such ways, the oxygen electrode method is able to measure the initial number of bacteria in a short time and accurately.

The oxygen electrode method such as is described in Japanese Patent Application Laid-Open No. 2000-287699 encounters a situation where a current value being measured does not decrease down to a threshold value or below depending on the combination of a medium and a bacterial strain. Such situation causes the occurrence of false detection such as a false negative and variations in detection times, resulting in a reduction in measurement accuracy.

Another problem of the conventional oxygen electrode methods is that fungi cannot be measured accurately because fungi have a slow respiration rate and thus when cultured in a typical manner, the oxygen concentration does not decrease rapidly. Further, fungi have a slow growth rate and can be determined by the conventional oxygen electrode methods only after growing for about a week, resulting in a prolonged measurement time.

SUMMARY OF THE INVENTION

Problems to be Solved by the Invention

It is an object of the present invention to provide a method and a device of measuring the number of bacteria capable of measuring the initial number of bacteria accurately and with reproducibility with an oxygen electrode method, and a cell used in the device. It is also an object of the invention to provide a method and a device of measuring the number of bacteria capable of measuring the initial number of bacteria for fungi accurately and in a significantly reduced measurement time, and a cell used in the device.

A method according to a first aspect of the present invention includes the steps of (a) adding a to-be-measured sample including a predetermined bacterial strain to a predetermined medium, (b) measuring a current value flowing through the medium added with the sample with an oxygen electrode at a predetermined temperature and at a predetermined constant voltage, (c) measuring time required for the current value that has decreased temporarily after starting the measurement of step (b) to increase thereafter to exceed a predetermined threshold value, and (d) calculating the initial number of bacteria of the bacterial strain included in the sample based on the time required.

The method of measuring the number of bacteria according to the first aspect of the present invention includes the steps of (a) adding a to-be-measured sample including a predetermined bacterial strain to a predetermined medium, (b) measuring a current value flowing through the medium added with the sample with an oxygen electrode at a predetermined temperature and at a predetermined constant voltage, (c) measuring time required for the current value that has decreased temporarily after starting the measurement of step (b) to increase thereafter to exceed a predetermined threshold value, and (d) calculating the initial number of bacteria of the bacterial strain included in the sample based on the time required. Therefore, the initial number of bacteria can be measured accurately and with reproducibility by utilizing a newly discovered phenomenon of a current value decreasing temporarily and increasing thereafter.

The method according to a second aspect of the present invention is the method of measuring the number of bacteria according to the first aspect of the present invention, wherein the current value decreases temporarily and increases thereafter due to metabolic activity of the bacterial strain included in the sample.

In the method of measuring the number of bacteria according to the second aspect of the present invention, the current value decreases temporarily and increases thereafter due to metabolic activity of the bacterial strain included in the sample. Therefore, the initial number of bacteria can be measured accurately and with reproducibility.

The method according to a third aspect of the present invention is the method of measuring the number of bacteria according to the first or second aspect of the present invention, wherein the medium is a medium used for a specific enzyme substrate culture medium method, and the bacterial strain is one of *Escherichia coli* and coliform bacteria.

In the method of measuring the number of bacteria according to the third aspect of the present invention, the medium is a medium used for a specific enzyme substrate culture medium method, and the bacterial strain is one of *Escherichia coli* and coliform bacteria. Therefore, the initial number of bacteria can be measured accurately and with reproducibility by utilizing the newly discovered phenomenon of a current value decreasing temporarily and increasing thereafter.

The method according to a fourth aspect of the present invention is the method of measuring the number of bacteria according to the first or second aspect of the present invention, wherein the medium is a PYG medium, and the bacterial strain is a fungus.

In the method of measuring the number of bacteria according to the fourth aspect of the present invention, the medium is a PYG medium, and the bacterial strain is a fungus. Therefore, the initial number of bacteria can be measured accurately and with reproducibility by utilizing the newly discovered phenomenon of a current value decreasing temporarily and increasing thereafter. Further, utilizing the newly discovered phenomenon, the method of measuring the number of bacteria according to the fourth aspect of the present invention allows a significant reduction in measurement time from conventional methods.

A device according to a fifth aspect of the present invention includes a cell holding a to-be-measured sample including a predetermined bacterial strain and a predetermined medium, an oxygen electrode provided in the cell, a current measurement unit measuring a current value flowing through the medium added with the sample with the oxygen electrode at a predetermined temperature and at a predetermined constant voltage, a required time measurement unit measuring time required for the current value that has decreased temporarily after starting the measurement at the current measurement unit to increase thereafter to exceed a predetermined threshold value, and a bacteria-number calculation unit calculating the initial number of bacteria of the bacterial strain included in the sample based on the time required.

The device of measuring the number of bacteria according to the fifth aspect of the present invention includes a cell holding a to-be-measured sample including a predetermined bacterial strain and a predetermined medium, an oxygen electrode provided in the cell, a current measurement unit measuring a current value flowing through the medium added with the sample with the oxygen electrode at a predetermined temperature and at a predetermined constant voltage, a required time measurement unit measuring time required for the current value that has decreased temporarily after starting the measurement at the current measurement unit to increase thereafter to exceed a predetermined threshold value, and a bacteria-number calculation unit calculating the initial number of bacteria of the bacterial strain included in the sample based on the time required. Therefore, the initial number of bacteria can be measured accurately and with reproducibility by utilizing the newly discovered phenomenon of a current value decreasing temporarily and increasing thereafter.

The device according to a sixth aspect of the present invention is the device of measuring the number of bacteria according to the fifth aspect of the present invention, wherein the current value decreases temporarily and increases thereafter due to metabolic activity of the bacterial strain included in the sample.

In the device of measuring the number of bacteria according to the sixth aspect of the present invention, the current value decreases temporarily and increases thereafter due to metabolic activity of the bacterial strain included in the sample. Therefore, the initial number of bacteria can be measured accurately and with reproducibility.

The device according to a seventh aspect of the present invention is the device of measuring the number of bacteria according to the fifth or sixth aspect of the present invention, wherein the medium is a medium used for a specific enzyme substrate culture medium method, and the bacterial strain is one of *Escherichia coli* and coliform bacteria.

In the device of measuring the number of bacteria according to the seventh aspect of the present invention, the medium is a medium used for a specific enzyme substrate culture medium method, and the bacterial strain is one of *Escherichia coli* and coliform bacteria. Therefore, the initial number of bacteria can be measured accurately and with reproducibility by utilizing the newly discovered phenomenon of a current value decreasing temporarily and increasing thereafter.

The device according to an eighth aspect of the present invention is the device of measuring the number of bacteria according to the fifth or sixth aspect of the present invention, wherein the medium is a PYG medium, and the bacterial strain is a fungus.

In the device of measuring the number of bacteria according to the eighth aspect of the present invention, the medium is a PYG medium, and the bacterial strain is a fungus. Therefore, the initial number of bacteria can be measured accurately and with reproducibility by utilizing the newly discovered phenomenon of a current value decreasing temporarily and increasing thereafter. Further, utilizing the newly discovered phenomenon, the device of measuring the number of bacteria according to the eighth aspect of the present invention allows a significant reduction in measurement time from conventional methods.

A cell according to a ninth aspect of the present invention is a cell holding a to-be-measured sample including a predetermined bacterial strain and a predetermined medium, including an oxygen electrode on an inner wall of the cell, the oxygen electrode being capable of measuring a current value flowing through the medium at a predetermined temperature and at a predetermined constant voltage, the current value decreasing temporarily and increasing thereafter.

The cell according to the ninth aspect of the present invention holds a to-be-measured sample including a predetermined bacterial strain and a predetermined medium, including an oxygen electrode on an inner wall of the cell, the oxygen electrode being capable of measuring a current value flowing through the medium at a predetermined temperature and at a predetermined constant voltage, the current value decreasing temporarily and increasing thereafter. Therefore, the initial number of bacteria can be measured accurately and with reproducibility by utilizing the newly discovered phenomenon of a current value decreasing temporarily and increasing thereafter.

The cell according to a tenth aspect of the present invention is the cell according to the ninth aspect of the present invention, wherein the current value decreases temporarily and increases thereafter due to metabolic activity of the bacterial strain included in the sample.

In the cell according to the tenth aspect of the present invention, the current value decreases temporarily and increases thereafter due to metabolic activity of the bacterial strain included in the sample. Therefore, the initial number of bacteria can be measured accurately and with reproducibility.

The cell according to an eleventh aspect of the present invention is the cell according to the ninth or tenth aspect of the present invention, wherein the medium is a medium used for a specific enzyme substrate culture medium method, and the bacterial strain is one of *Escherichia coli* and coliform bacteria.

In the cell according to the eleventh aspect of the present invention, the medium is a medium used for a specific enzyme substrate culture medium method, and the bacterial strain is one of *Escherichia coli* and coliform bacteria. Therefore, the initial number of bacteria can be measured accurately and with reproducibility by utilizing the newly discovered phenomenon of a current value decreasing temporarily and increasing thereafter.

The cell according to a twelfth aspect of the present invention is the cell according to the ninth or tenth aspect of the present invention, wherein the medium is a PYG medium, and the bacterial strain is a fungus.

In the cell according to the twelfth aspect of the present invention, the medium is a PYG medium, and the bacterial strain is a fungus. Therefore, the initial number of bacteria can be measured accurately and with reproducibility by utilizing the newly discovered phenomenon of a current value decreasing temporarily and increasing thereafter. Further, utilizing the newly discovered phenomenon, the cell according to the twelfth aspect of the present invention allows a significant reduction in measurement time from conventional methods.

These and other objects, features, aspects and advantages of the present invention will become more apparent from the following detailed description of the present invention when taken in conjunction with the accompanying drawings.

BRIEF DESCRIPTION OF DRAWINGS

FIGS. 4 and 5 are diagrams illustrating variations in current value of the device of measuring the number of bacteria according to the first preferred embodiment.

FIGS. 7 and 8 are diagrams illustrating variations in current value of the device of measuring the number of bacteria according to the first preferred embodiment.

FIG. 9 is a diagram illustrating variations in current value of a device of measuring the number of bacteria according to a second preferred embodiment.

BEST MODE FOR CARRYING OUT THE INVENTION

In the oxygen electrode method, dissolved oxygen concentration decreases due to respiration (metabolic activity) of a bacterial strain, which involves a reduction in current value flowing between a working electrode and a counter electrode forming an oxygen electrode (hereafter simply called a current value). A "bacterial strain" herein refers to a cellular strain that includes bacteria or fungus. A new phenomenon was discovered, however, in which the current value being measured decreases temporarily with the metabolic activity and increases rapidly thereafter, when a specific medium and a specific bacterial strain are combined. The present invention is directed at a method of measuring the number of bacteria, a device of measuring the number of bacteria and a cell used in the device utilizing this phenomenon in the oxygen electrode method.

Preferred embodiments will be described by citing concrete names of the specific culture and the specific bacterial strain. Yet it is appreciated that the concrete names are not intended to limit the scope of the present invention.

First Preferred Embodiment

In this embodiment, a medium used for a specific enzyme substrate culture medium method (hereafter simply called a specific enzyme substrate culture medium) is used as the specific medium. Colilert (registered trademark), which contains 4-methylumbelliferyl-β-d-glucuronide (mug), is one example of the specific enzyme substrate culture medium. In this embodiment, *Escherichia coli* or coliform bacteria are used as the specific bacterial strain. Also in this embodiment, stainless steel (SUS) is used for the base material of the oxygen electrode.

Figure 1:
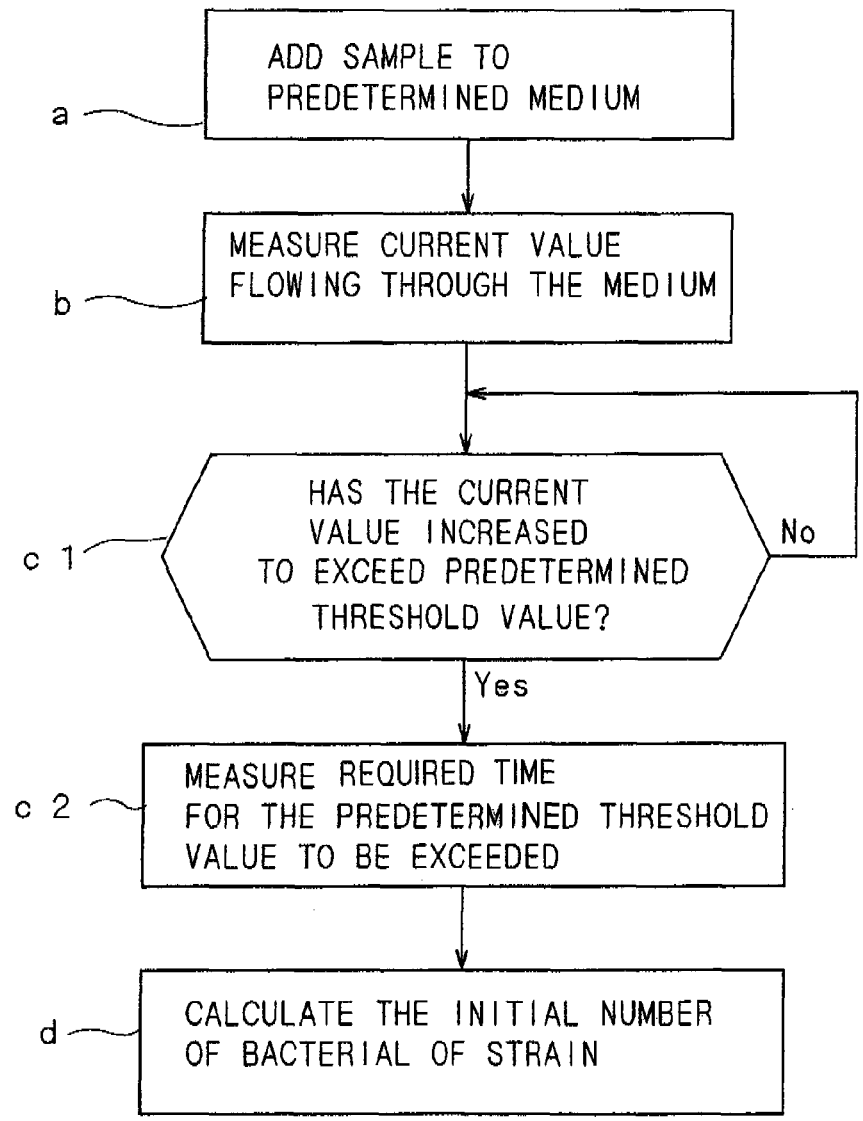
FIG. 1 is a flowchart of a method of measuring the number of bacteria according to a first preferred embodiment.

A method of measuring the number of bacteria used for the above combination is described. FIG. 1 is a flowchart illustrating the method of measuring the number of bacteria according to this embodiment. First, in step a, a sample (specimen) including *Escherichia coli* or coliform bacteria is added to the specific enzyme substrate culture medium. More specifically, the specific enzyme substrate culture medium is liquid, and the sample including *Escherichia coli* or coliform bacteria is pulverized and stirred by Stomacher, to be added to the liquid medium.

Figure 2:
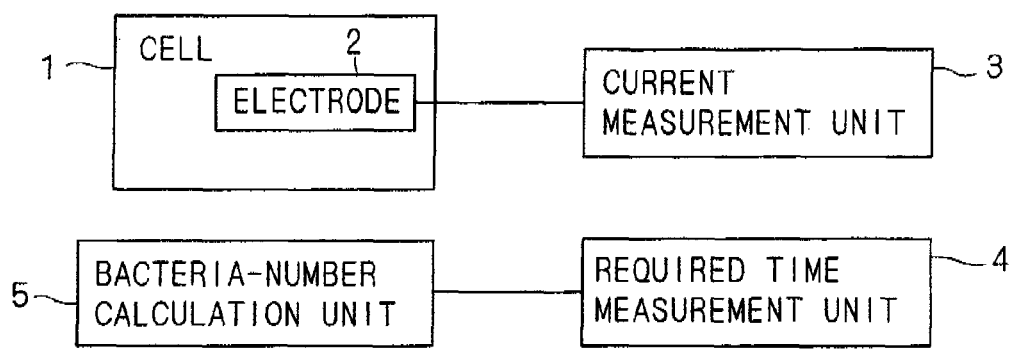
FIG. 2 is a block diagram of a device of measuring the number of bacteria according to the first preferred embodiment.
Figure 3:
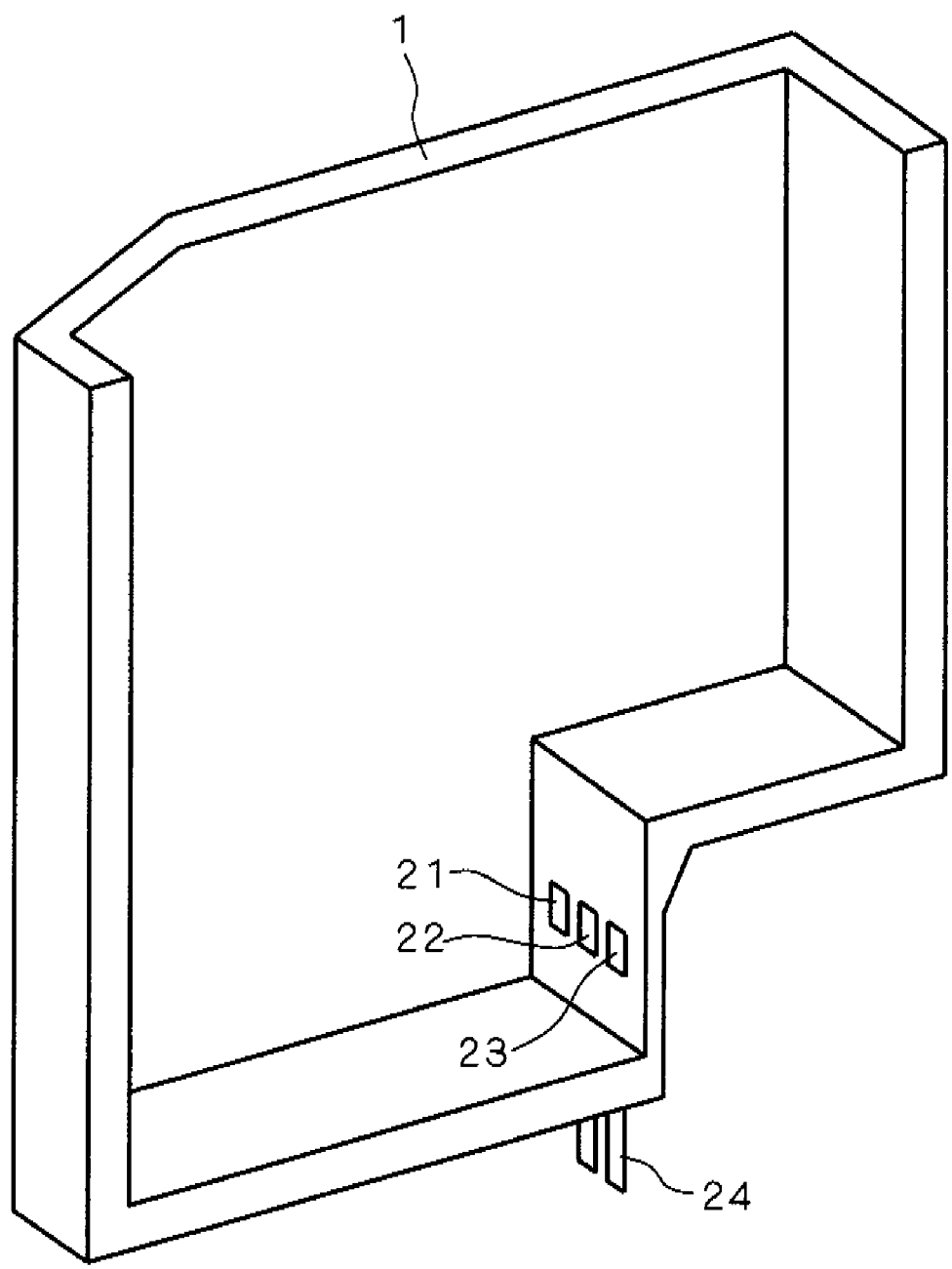
FIG. 3 is a sectional perspective diagram of a cell according to the first preferred embodiment.

Next, in step b, a current value flowing through the medium added with the sample is measured. The current value measurement is carried out at a predetermined temperature under temperature control, and at a predetermined constant voltage. FIG. 2 is a block diagram of the device of measuring the number of bacteria according to this embodiment. This device of measuring the number of bacteria is provided with a cell 1 that holds the medium added with the sample. The cell 1 has an oxygen electrode 2 provided therein which is used for the oxygen electrode method. FIG. 3 is a sectional perspective diagram of the cell 1. Provided on a side wall near the bottom of the cell 1 are three electrodes forming the oxygen electrode 2, i.e. a counter electrode 21, a working electrode 22, and a reference electrode 23. The cell 1 is further provided with an output terminal 24 electrically connected to the counter electrode 21, the working electrode 22, and the reference electrode 23. The oxygen electrode 2 is connected to a current measurement unit 3 through the output terminal 24.

The structure of the counter electrode 21, the working electrode 22, and the reference electrode 23 is described. Stainless steel is used for the electrode base material of the counter electrode 21, the working electrode 22, and the reference electrode 23. The surface of this electrode base material is plated with gold. The electrode base material of the oxygen electrode 2 used in the present invention is not limited to stainless steel but may be other metal materials (such as copper). The surface of the electrode base material of other metal materials is likewise plated with gold.

The current measurement unit 3 in FIG. 2 measures the current value flowing through the medium added with the sample with the oxygen electrode 2 (step b). The counter electrode 21 and the working electrode 22 are particularly used to measure the current flowing through the medium. The current flowing through the medium is a current that flows when dissolved oxygen in the medium is reduced to water at the working electrode 22, as was described in the background art section. Accordingly, the current value is high with high dissolved oxygen concentration in the medium, and the current value becomes low with low dissolved oxygen concentration. Meanwhile, *Escherichia coli* or coliform bacteria included in the sample grow while increasing the amount of oxygen consumed. Accordingly, the dissolved oxygen concentration in the medium decreases, causing the current value to decrease as well. In the conventional oxygen electrode method, therefore, time (hereafter also called the time required) required for the reducing current value and a threshold value to cross each other can be determined by setting the threshold value to a current value near zero (e.g. 100 nA).

However, it was newly discovered that a phenomenon different from the background art occurs when *Escherichia coli* or coliform bacteria in the specific enzyme substrate culture medium is measured with an oxygen electrode as a combination of the specific medium and the specific bacterial strain. FIG. 4 is a graph demonstrating variations in current value according to this embodiment. In FIG. 4, coliform bacteria in the specific enzyme substrate culture medium (Colilert) are measured with the oxygen electrode. In the current value variations of FIG. 4, a current value of about 1000 nA flows with stability between the start of the measurement and the point of about 400 minutes, but with the dissolved oxygen concentration starting to decrease due to the growth of the coliform bacteria, the current value decreases thereafter down to about 650 nA at the point of about 500 minutes of measurement time. Then, the current value starts to increase rapidly, up to about 2000 nA at the point of about 580 minutes of measurement time. Since oxygen included in the medium at the start of the measurement is in saturation, an inflow of oxygen from the outside has little influence on the increase in current value. With the current value variations such as shown in FIG. 4, the time required cannot be measured by setting the threshold value to the conventional current value near zero (e.g. 100 nA).

Therefore, in this embodiment, the threshold value is set to a current value higher than that at the start of the measurement so that the time required can be measured when a current value decreases temporarily and increases thereafter. In FIG. 4, the threshold value is set to 1500 nA, and the current value exceeds the threshold value at the point of about 540 minutes. This means the time required shown in FIG. 4 is about 540 minutes. In the flowchart shown in FIG. 1, it is determined whether the current value has increased and exceeded the threshold value in step c1 and, when it is determined that the current value has exceeded the threshold value in step c1, the time required is measured in step c2. The time required is measured at a required time measurement unit 4 of the device of measuring the number of bacteria shown in FIG. 2. In the course of performing step b, step c1 and step c2, *Escherichia coli* or coliform bacteria is cultured at about 30° C.

Figure 5:
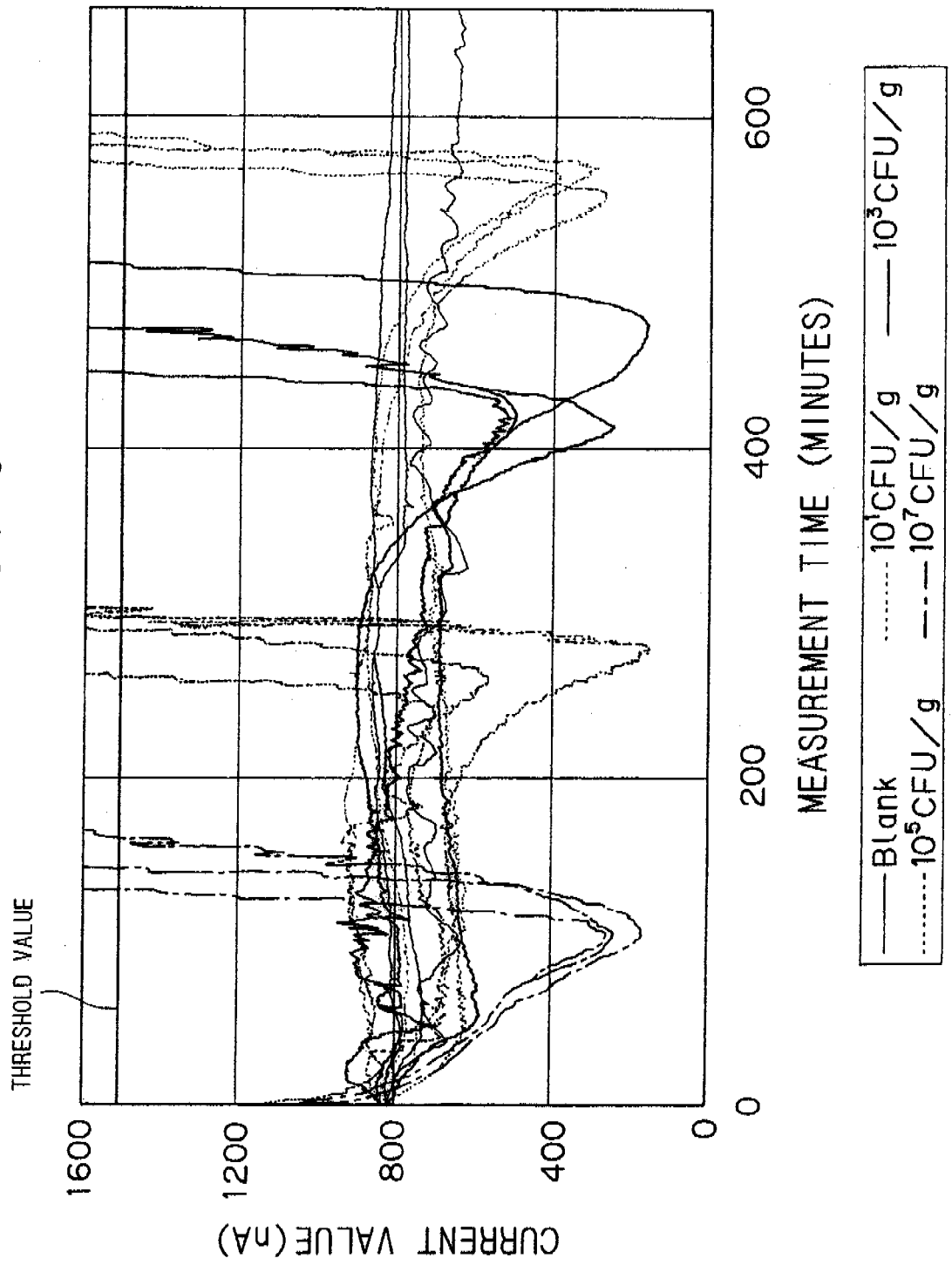
Figure 6:
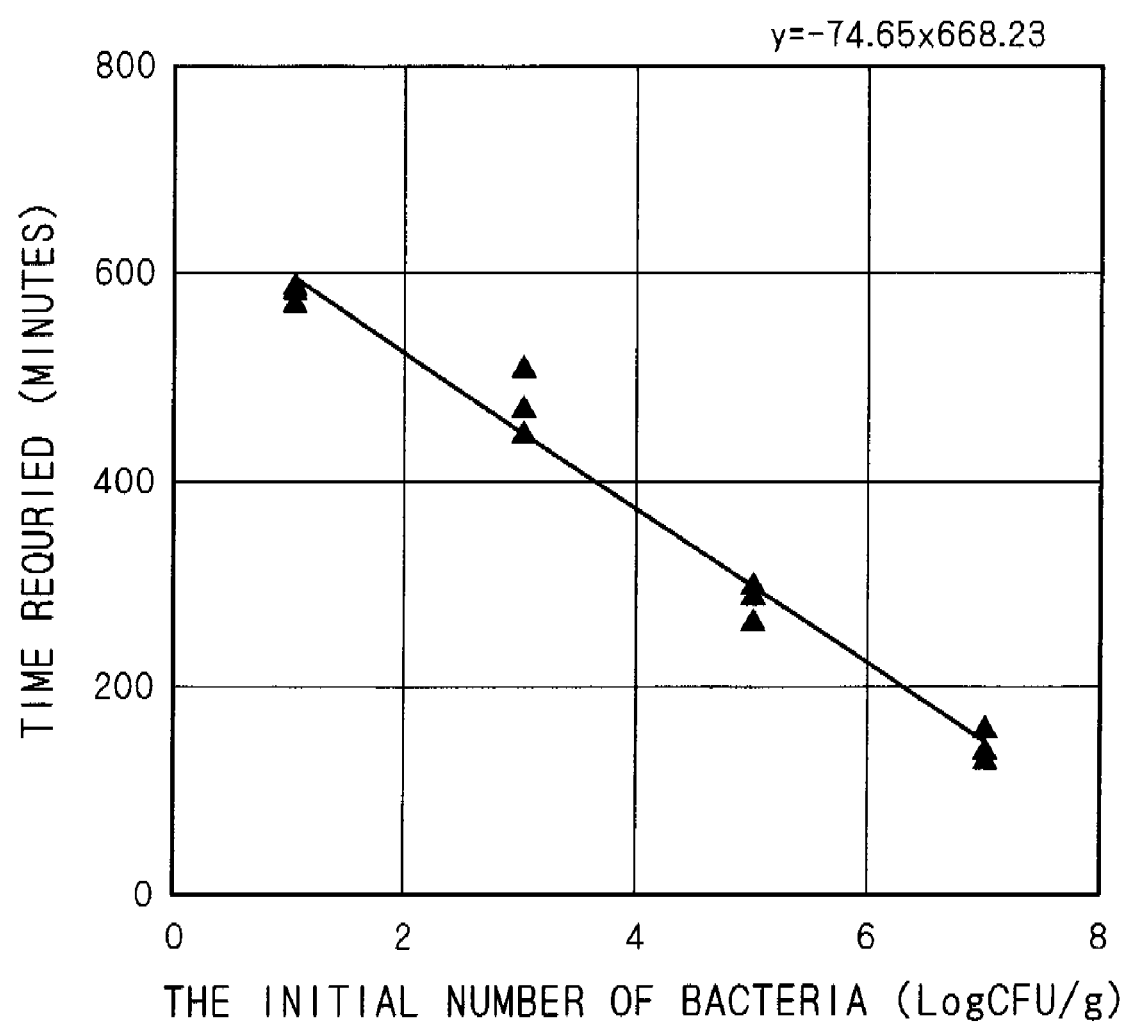
FIG. 6 is a diagram illustrating a calibration curve of the device of measuring the number of bacteria according to the first preferred embodiment.

Next, in step d shown in FIG. 1, the initial number of bacteria included in the sample is calculated. The initial number of bacteria included in the sample is calculated based on the measured time required at a bacteria-number calculation unit 5 of the device of measuring the number of bacteria shown in FIG. 2. To calculate the initial number of bacteria, a calibration curve needs to be obtained in advance, as was described in the background art section. This will be described with reference to a specific example. First, variations in current value are measured for samples with known initial numbers of bacteria. FIG. 5 demonstrates current value variations in samples with known initial numbers of bacteria. In FIG. 5, five types of samples with initial numbers of bacteria of 0, $10^1$, $10^3$, $10^5$, and $10^7$ (unit: CFU/g) are measured, with three of them being measured for each type. Then, the time required is measured and plotted from FIG. 5 with the threshold value being set to 1500 nA, to obtain a graph of a calibration curve shown in FIG. 6. In FIG. 6, the horizontal axis represents the initial number of bacteria (LogCFG/g), and the vertical axis represents the measurement time (the time required). Applying the least squares method to the time required data plotted in FIG. 6, a calibration curve of "measurement time (y)=−74.65×the initial number of bacteria (x)+ 668.23" is obtained.

A sample with an unknown initial number of bacteria is measured using the calibration curve obtained as above. First, variations in current value are measured for the sample with an unknown initial number of bacteria, to obtain the time required. Then, the obtained time required is applied to the calibration curve shown in FIG. 6, to calculate the initial number of bacteria. Since the time required obtained from the graph shown in FIG. 4 is about 540 minutes, 540 is substituted in the variable y to obtain the variable x. The resultant variable x is about 1.72, which leads to the initial number of bacteria of $10^{1.72}$ (CFU/g). The calibration curve that needs to be obtained in advance in order to measure the initial number of bacteria in step d cannot be used for a different bacterial strain and the like. A calibration curve thus needs to be prepared for each of necessary bacterial strains and the like. FIG. 5 shows the measurement of coliform bacteria, and FIG. 6 shows the calibration curve for coliform bacteria.

As has been described, it was newly discovered that a phenomenon different from the background art occurs when *Escherichia coli* or coliform bacteria in the specific enzyme substrate culture medium is measured with an oxygen electrode as a combination of the specific medium and the specific bacterial strain. Namely, a phenomenon in which dissolved oxygen concentration in a medium decreases due to respiration of *Escherichia coli* or coliform bacteria, which involves a reduction in current value, but the current value increases thereafter. The detailed mechanism of the phenomenon is not known at this stage. It is only confirmed that the phenomenon has reproducibility when a specific medium (specific enzyme substrate culture medium) and a specific bacterial strain (*Escherichia coli* or coliform bacteria) are combined and measured.

Figure 7:
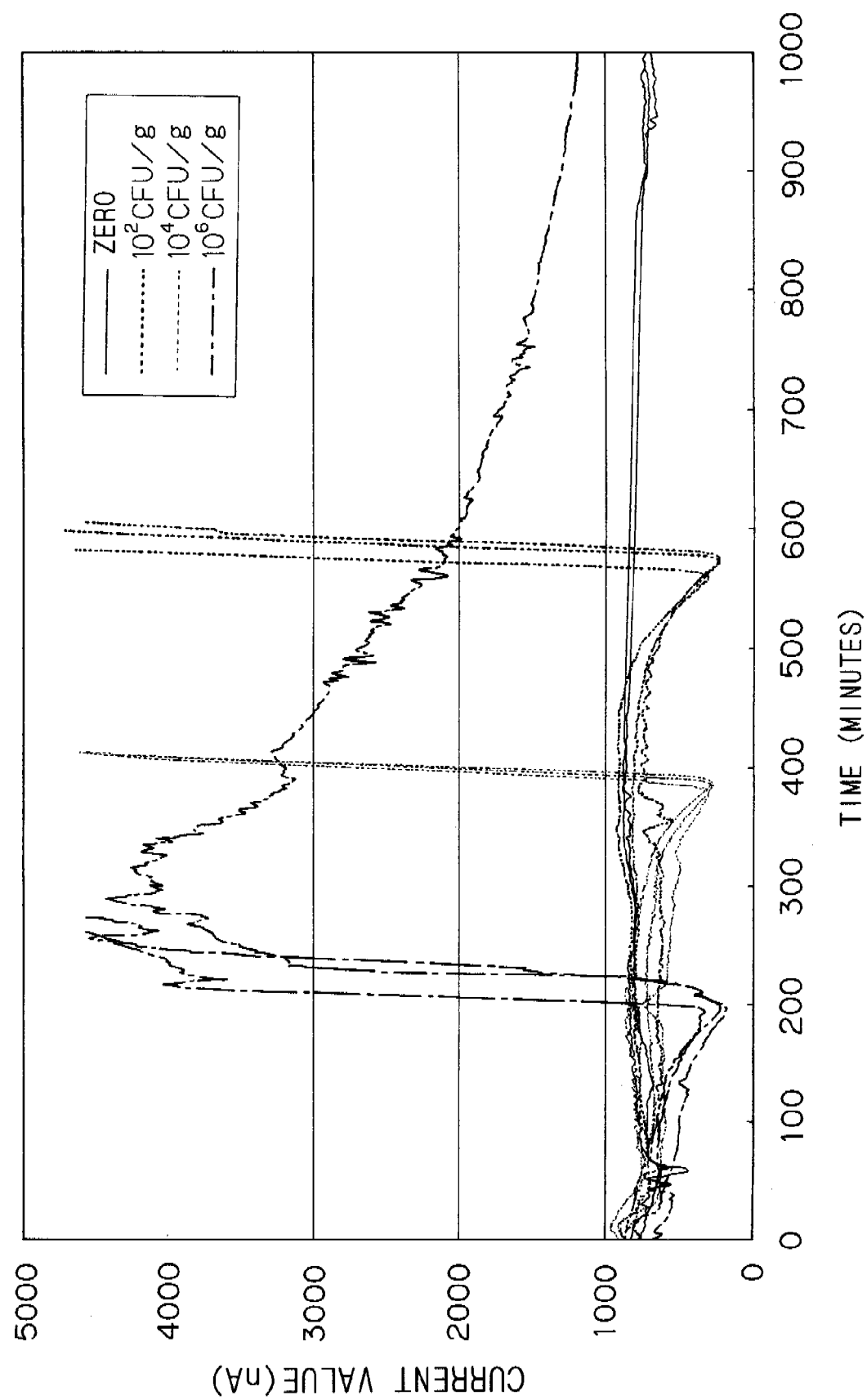

Although the detailed mechanism is unknown, the above phenomenon occurs when a specific medium and a specific bacterial strain are combined even with a change in electrode base material. FIGS. 7 and 8 illustrate measurement results with the same medium and the same bacterial strain but different electrode base materials. In FIGS. 7 and 8, the horizontal axis represents the measurement time (minutes), and the vertical axis represents a current value (nA). In FIG. 7, Colilert is used as the specific medium, coliform bacteria as the specific bacterial strain, and stainless steel as the electrode base material. In FIG. 8, on the other hand, Colilert is used as the specific medium, coliform bacteria as the specific bacterial strain, and copper as the electrode base material. And in FIGS. 7 and 8, four types of samples with initial numbers of bacteria of 0, $10^2$, $10^4$, and $10^6$ (unit: CFU/g) are measured, with three of them being measured for each type. As can be appreciated from FIGS. 7 and 8, the results indicate that the phenomenon of a current value decreasing temporarily and increasing thereafter occurs when the medium of Colilert and the bacterial strain of coliform bacteria are combined, regardless of the difference between stainless steel and copper for the electrode base material. It is shown from a comparison of FIGS. 7 and 8 that current rises are apparently steeper with less variation in FIG. 7. Namely, the use of stainless steel instead of copper for the electrode base material reduces the measurement time and reduces measurement variations.

As described above, this embodiment includes the step (a) of adding the to-be-measured sample to the medium used for a specific enzyme substrate culture medium method, the step (b) of measuring the current value flowing through the medium added with the sample with the oxygen electrode, the step (c) of measuring the time required for the current value that has decreased temporarily due to metabolic activity of *Escherichia coli* or coliform bacteria included in the sample after starting the measurement of step (b) to increase thereafter to exceed the predetermined threshold value, and the step (d) of calculating the initial number of bacteria of the *Escherichia coli* or coliform bacteria included in the sample based on the time required. Therefore, the initial number of bacteria can be measured accurately and with reproducibility by utilizing the newly discovered phenomenon of a current value decreasing temporarily and increasing thereafter.

While the threshold value is set to a current value higher than that at the start of the measurement in this embodiment, the threshold value may be set to a current value lower than that at the start of the measurement in the present invention, provided that the point in time can be measured when a current value crosses the threshold value in an increase phase after a temporary decrease.

Second Preferred Embodiment

In this embodiment, a PYG (bacteriological peptone/yeast extract/glucose) medium is used as the specific medium, and a fungus as the specific bacterial strain. The fungus may be yeast, mold, or *Candida albicans* (IFO 1594), for example.

The method of measuring the number of bacteria used in the first preferred embodiment is applied to the above combination. The method of measuring the number of bacteria will thus be explained with reference to the flowchart shown in FIG. 1. Since fungi have a slow growth rate compared to *Escherichia coli* and the like, the following work is required as preliminary work, for example. First, a fungus (e.g. yeast) is isolated from a subcultured colony. Next, the fungus is adjusted to $1 \times 10^2$ CFU/ml of fungus liquid while being examined by a microscope. Then, the adjusted fungus liquid is inoculated into a fruit preparation. The inoculated sample (specimen) is then put in a constant temperature bath of 30° C. and precultured for two days. After that, in step a, 1 ml of the precultured sample is added to 1 ml of the Pyg medium.

Next, in step b, a current value flowing through the medium added with the sample is measured. A device of measuring the number of bacteria according to this embodiment is the same that was described in the first preferred embodiment, the block diagram of which is shown in FIG. 2. This device of measuring the number of bacteria is provided with the cell 1 that holds the medium added with the sample. The cell 1 has the oxygen electrode 2 provided therein which is used for the oxygen electrode method. The cell 1 according to this embodiment is also the same that was described in the first preferred embodiment, the sectional perspective diagram of which is shown in FIG. 3. Provided on the side wall near the bottom of the cell 1 are the three electrodes forming the oxygen electrode 2, i.e. the counter electrode 21, the working electrode 22, and the reference electrode 23. Stainless steel is used for the electrode base material of the counter electrode 21, the working electrode 22, and the reference electrode 23. The surface of this electrode base material is plated with gold. The electrode base material of the oxygen electrode 2 used in the present invention is not limited to stainless steel but may be other metal materials (such as copper). The surface of the electrode base material of other metal materials is likewise plated with gold. The cell 1 is further provided with the output terminal 24 electrically connected to the counter electrode 21, the working electrode 22, and the reference electrode 23. The counter electrode 21, the working electrode 22, and the reference electrode 23 are connected to the current measurement unit 3 shown in FIG. 2 through the output terminal 24.

The current measurement unit 3 in FIG. 2 measures the current flowing through the medium with the counter electrode 21 and the working electrode 22. Again in this embodiment, the current value decreases with the fungus consuming the dissolved oxygen in the medium, and increases thereafter. Such phenomenon of current value variations is the same as the phenomenon of current value variations for coliform bacteria as shown in FIG. 4. Just like the coliform bacteria case, the detailed mechanism of such phenomenon is not known at this stage. FIG. 9 is a graph demonstrating variations in current value for fungi. FIG. 9 shows current value variations for three types of fungi, i.e. ingredient separation yeast, *Candida albicans*, and ingredient separation mold. In FIG. 9, the horizontal axis represents the measurement time (minutes), and the vertical axis represents a current value (nA).

First, the ingredient separation yeast hardly decreases in current value, and increases rapidly thereafter. The ingredient separation yeast crosses a threshold value, which is set to 1500 nA as in the first preferred embodiment, after a lapse of about 20 minutes (0.33 hour). It is therefore shown that the time required for the ingredient separation yeast is about 20 minutes. Second, *Candida albicans* decreases slightly in current value, and increases rapidly thereafter. *Candida albicans* crosses the threshold value after a lapse of about 30 minutes (0.5 hour), which shows that the time required is about 30 minutes. Third, the ingredient separation mold decreases temporarily in current value, and increases thereafter. The ingredient separation mold crosses the threshold value after a lapse of about 135 minutes (2.25 hour), which shows that the time required is about 135 minutes. FIG. 9 also shows variations in current value measured for a cell that includes no fungus (blank cell). The blank cell gently decreases in current value with measurement time without changing rapidly.

The time required is measured at the required time measurement unit 4 shown in FIG. 2. In the flowchart shown in FIG. 1, it is determined whether the current value has increased and exceeded the threshold value in step c1 and, when it is determined that the current value has exceeded the threshold value, the time required is measured in step c2. In the course of performing step b, step c1 and step c2, the fungus is cultured at about 30° C.

Next, in step d, the initial number of bacteria included in the sample is calculated based on the calculated time required. This is carried out at the bacteria-number calculation unit 5 in the device of measuring the number of bacteria shown in FIG. 2. To calculate the initial number of bacteria, a calibration curve needs to be obtained in advance as in the first preferred embodiment. The way a calibration curve is obtained was specifically discussed in the first preferred embodiment and a discussion of the way is not replicated below. Using the calibration curve obtained in advance, the initial number of bacteria for the fungus is calculated based on the calculated time required. The necessary time to obtain the initial number of bacteria for the fungus is about one day that includes the time of setting the sample in the cell and the time required for measurement. Thus in this embodiment, the initial number of bacteria for the fungus can be obtained in about three days that includes two days of preculture as well, which allows a significant reduction in time from about one week that has been conventionally required.

As described above, this embodiment includes the step (a) of adding the to-be-measured sample to the PYG medium, the step (b) of measuring the current value flowing through the medium added with the sample with the oxygen electrode, the step (c) of measuring the time required for the current value that has decreased temporarily due to metabolic activity of the fungus included in the sample after starting the measurement to increase thereafter to exceed the predetermined threshold value, and the step (d) of calculating the initial number of bacteria for the fungus included in the sample based on the time required. Therefore, the initial number of bacteria can be measured accurately and with reproducibility by utilizing the newly discovered phenomenon of a current value decreasing temporarily and increasing thereafter.

Further in this embodiment, the appropriate combination as described above is selected to utilize the newly discovered phenomenon of current value increase, thereby measuring fungus which have conventionally been unable to be measured accurately. Still further in the embodiment, fungi can be determined within three days that includes about two days of preculture as well, as opposed to the conventional determination after growing fungi for about one week.

What is claimed is:

1. A method of measuring the number of fungus cells, comprising the steps of:
   (a) adding a sample including said fungus to a PYG (bacteriological peptone/yeast extract/glucose) medium;
   (b) measuring a current value flowing through said medium added with said sample with an oxygen electrode at a predetermined temperature and at a predetermined constant voltage;
   (c) measuring time required for said current value that has decreased temporarily after starting the measurement of step (b) to increase thereafter to exceed a predetermined threshold value; and
   (d) calculating the initial number of said fungus included in said sample based on said time required.

2. The method of measuring the number of fungus cells according to claim 1, wherein
   said current value decreases temporarily and increases thereafter due to metabolic activity of said fungus included in said sample.

3. A method of measuring the number of bacteria, comprising the steps of:
   (a) adding a sample including one of *Escherichia coli* and coliform bacteria to a medium that contains 4-methylumbelliferyl-β-D-glucuronide (MUG);
   (b) measuring a current value flowing through said medium added with said sample with an oxygen electrode at a predetermined temperature and at a predetermined constant voltage;
   (c) measuring time required for said current value that has decreased temporarily after starting the measurement of step (b) to increase thereafter to exceed a predetermined threshold value; and
   (d) calculating the initial number of said one of *Escherichia coli* and coliform bacteria included in said sample based on said time required.

4. The method of measuring the number of bacteria according to claim 3, wherein
   said current value decreases temporarily and increases thereafter due to metabolic activity of said one of *Escherichia coli* and coliform bacteria included in said sample.

5. A device for measuring the number of fungus cells, comprising:
   a cell holding a sample including said fungus and a PYG (bacteriological peptone/yeast extract/glucose) medium;
   an oxygen electrode provided in said cell;
   a current measurement unit measuring a current value flowing through said medium added with said sample with said oxygen electrode at a predetermined temperature and at a predetermined constant voltage;
   a required time measurement unit measuring time required for said current value that has decreased temporarily after starting the measurement at said current measurement unit to increase thereafter to exceed a predetermined threshold value; and
   a calculation unit calculating the initial number of said fungus included in said sample based on said time required.

6. The device of measuring the number of fungus cells according to claim 5, wherein
   said current value decreases temporarily and increases thereafter due to metabolic activity of said fungus included in said sample.

7. A device for measuring the number of bacteria, comprising:
   a cell holding a sample including one of *Escherichia coli* and coliform bacteria and
   a medium that contains 4-methylumbelliferyl-β-d-glucuronide (mug);
   an oxygen electrode provided in said cell;
   a current measurement unit measuring a current value flowing through said medium added with said sample with said oxygen electrode at a predetermined temperature and at a predetermined constant voltage;
   a required time measurement unit measuring time required for said current value that has decreased temporarily after starting the measurement at said current measurement unit to increase thereafter to exceed a predetermined threshold value; and
   a bacteria-number calculation unit calculating the initial number of said one of *Escherichia coli* and coliform bacteria included in said sample based on said time required.

8. The device of measuring the number of bacteria according to claim 7, wherein
   said current value decreases temporarily and increases thereafter due to metabolic activity of said one of *Escherichia coli* and coliform bacteria included in said sample.

9. A cell holding a sample including fungus cells and a PYG (bacteriological peptone/yeast extract/glucose) medium, comprising:
   an oxygen electrode on an inner wall of said cell, said oxygen electrode being capable of measuring a current value flowing through said medium at a predetermined temperature and at a predetermined constant voltage, said current value decreasing temporarily and increasing thereafter.

10. The cell according to claim 9, wherein
    said current value decreases temporarily and increases thereafter due to metabolic activity of said fungus included in said sample.

11. A cell holding a sample including
    one of *Escherichia coli* and coliform bacteria and
    a medium that contains 4-methylumbelliferyl-β-d-glucuronide (mug), said cell comprising:
    an oxygen electrode on an inner wall of said cell, said oxygen electrode being capable of measuring a current value flowing through said medium at a predetermined temperature and at a predetermined constant voltage, said current value decreasing temporarily and increasing thereafter.

12. The cell according to claim 11, wherein
    said current value decreases temporarily and increases thereafter due to metabolic activity of said one of *Escherichia coli* and coliform bacteria included in said sample.

* * * * *